United States Patent
Pirkl et al.

(10) Patent No.: US 7,038,002 B2
(45) Date of Patent: May 2, 2006

(54) PRODUCTION OF MIXTURES OF DIISOCYANATES AND POLYISOCYANATES FROM THE DIPHENYLMETHANE SERIES WITH HIGH CONTENTS OF 4,4'-METHYLENEDIPHENYL DIISOCYANATE AND 2,4'-METHYLENEDIPHENYL DIISOCYANATE

(75) Inventors: Hans-Georg Pirkl, Leverkusen (DE);
Ulrich Liman, Langenfeld (DE);
Robert Vieler, Dormagen (DE); Ralf Echterhoff, Dormagen (DE)

(73) Assignee: Bayer Materialscience AG, Leverkusen (DE)

( * ) Notice: Subject to any disclaimer, the term of this patent is extended or adjusted under 35 U.S.C. 154(b) by 0 days.

(21) Appl. No.: 10/896,129

(22) Filed: Jul. 21, 2004

(65) Prior Publication Data
US 2005/0020797 A1  Jan. 27, 2005

(30) Foreign Application Priority Data
Jul. 25, 2003  (DE)  ................................ 103 33 929

(51) Int. Cl.
*C08G 18/00* (2006.01)
*C08G 18/32* (2006.01)

(52) U.S. Cl. ............................ 528/44; 528/52; 528/85; 528/269; 560/347; 560/358; 560/359

(58) Field of Classification Search .................. 528/44, 528/52, 269, 85; 560/347, 358, 359
See application file for complete search history.

(56) References Cited

U.S. PATENT DOCUMENTS

| | | | |
|---|---|---|---|
| 3,471,543 A | 10/1969 | Sayigh | ........................ 260/453 |
| 3,793,362 A | 2/1974 | Kolakowski et al. | .. 260/453 SP |
| 3,799,963 A | 3/1974 | Adams | ................... 260/453 SP |
| 3,857,871 A | 12/1974 | Hatfield, Jr. et al. | ... 260/453 SP |
| 3,887,502 A | 6/1975 | Adams | ................... 260/2.5 AT |

(Continued)

FOREIGN PATENT DOCUMENTS

CA    1 137 514    12/1982

(Continued)

OTHER PUBLICATIONS

Manfred Stepanski and Peter Faessler, "New Hybrid Process for Purification and Separation of MDI Isomers", pp. 594-600.

*Primary Examiner*—Duc Truong
(74) *Attorney, Agent, or Firm*—Joseph C. Gil; Lyndanne M. Whalen

(57) ABSTRACT

A fraction of diisocyanates of the diphenylmethane series containing at least 95 wt. % binuclear methylenediphenyl diisocyanate is obtained by
a) reacting aniline and formaldehyde in the presence of an acid catalyst to produce diamines and polyamines of the diphenylmethane series containing binuclear methylenediphenyl diamine,
b) phosgenating the diamines and polyamines produced in a), optionally in the presence of a solvent, to produce a crude diisocyanate and polyisocyanate, and
c) separating a fraction containing at least 95 wt. % binuclear methylenediphenyl diisocyanate with a 4,4'-MDI content of over 60 wt. %, a 2,4'-MDI content of 4 to 35 wt. % and a 2,2'-MDI content of 0.01 to 10 wt. %, relative to the mass of the fraction, and a maximum of 20 ppm phenyl isocyanate and optionally a maximum of 50 ppm solvent from the crude diisocyanate and polyisocyanate produced in b) in a single distillation step with optional upstream and/or downstream separation of low-boiling components.

11 Claims, 2 Drawing Sheets

Binuclear content

U.S. PATENT DOCUMENTS

| | | | |
|---|---|---|---|
| 3,912,600 A | 10/1975 | Hatfield, Jr. et al. | 203/73 |
| 3,925,437 A | 12/1975 | Rowton | 260/453 SP |
| 4,189,443 A | 2/1980 | Eifler et al. | 260/453 PH |
| 4,414,074 A | 11/1983 | Ellendt et al. | 203/21 |
| 4,597,909 A | 7/1986 | Keggenhoff et al. | 560/347 |
| 5,179,227 A | 1/1993 | Ishida et al. | 560/352 |
| 5,258,417 A | 11/1993 | Narayan | 521/160 |
| 6,433,219 B1 | 8/2002 | Ströfer et al. | 560/347 |
| 6,437,073 B1 * | 8/2002 | Gunatillake et al. | 528/28 |
| 6,831,192 B1 | 12/2004 | Ströfer et al. | 560/347 |
| 2002/0132953 A1 | 9/2002 | Strofer et al. | 528/44 |

FOREIGN PATENT DOCUMENTS

| | | |
|---|---|---|
| DE | 271 820 | 9/1989 |
| GB | 1114690 | 5/1968 |
| GB | 1 3662 708 | 8/1974 |
| GB | 1 569 226 | 6/1980 |

* cited by examiner

PRODUCTION OF MIXTURES OF DIISOCYANATES AND POLYISOCYANATES FROM THE DIPHENYLMETHANE SERIES WITH HIGH CONTENTS OF 4,4'-METHYLENEDIPHENYL DIISOCYANATE AND 2,4'-METHYLENEDIPHENYL DIISOCYANATE

BACKGROUND OF THE INVENTION

The present invention relates to a process for the production of mixtures of diisocyanates and polyisocyanates from the diphenylmethane series with high contents of 4,4'- and 2,4'-methylenediphenyl diisocyanate and to the use of such mixtures for the production of polymers.

It is known that diisocyanates and polyisocyanates from the diphenylmethane series (MDI) are produced by phosgenating the corresponding diamines and polyamines from the diphenylmethane series (MDA). The diamines and polyamines from the diphenylmethane series are themselves produced by condensation of aniline and formaldehyde. By phosgenating the diamines from the diphenylmethane series the corresponding diisocyanates 2,2'-MDI, 2,4'-MDI and 4,4'-MDI which people skilled in the art describe as binuclear MDI (diisocyanates from the diphenylmethane series) are obtained. During the condensation of aniline and formaldehyde, the binuclear MDA (methylenediphenyl diamine MDA) also reacts further with formaldehyde and aniline, however, to produce higher-nuclear MDA grades, which after phosgenation represent the polynuclear content in the polymeric MDI (polyisocyanates from the diphenylmethane series). For many practical product applications it is preferable to obtain a high proportion of binuclear MDI. According to the current prior art this can be achieved in two different ways.

1. Aniline is used in large excess in the acid-catalyzed condensation of aniline and formaldehyde, the excess aniline is separated off from the reaction mixture and recycled. The large excess of aniline during the condensation produces an MDA mixture with a high proportion of binuclear MDA. The higher the ratio of aniline/formaldehyde used in the reaction, the higher the binuclear content contained in the reaction product. The ratio of 2,4'-MDA to 4,4'-MDA can also be influenced by the concentration of acid catalyst. High catalyst concentrations favor 4,4'-MDA. Low concentrations favor 2,4'-MDA. (See, e.g., EP-158059-B1 and EP-3303-B1.) Such MDA grades are referred to below as polymer A or polymer B grades for MDI-compositions comprising low 2,4'-isomer content or high 2,4'-isomer content, respectively. The desired MDI composition can be obtained by phosgenation of the MDA grades selectively produced in advance.

2. Polymeric MDA is produced in the conventional way from aniline and formaldehyde using an acid catalyst. The polymeric MDA is phosgenated and broken down by distillation into a highly monomer-rich and a polymer-rich fraction. The polymeric MDI fraction can be used as a commercial polymeric MDI product. The monomeric MDI fraction is broken down according to the prior art by distillation or by crystallization into the isomers 4,4'-MDI and a mixture of approximately 50% 2,4'-MDI and 50% 4,4'-MDI. The two monomeric products are sold or processed further to produce mixed products with polymeric MDI having high contents of binuclear MDI and in the correct isomer ratio.

In both cases, the investment and energy consumption involved mean that the cost of producing MDI mixtures having a high proportion of binuclear MDI is considerable.

In the first case, in the condensation of aniline and formaldehyde large excesses of aniline must be circulated, separated from the reaction mixture by distillation and then recycled.

In the second case, the condensation of aniline and formaldehyde with lower excesses of aniline produces considerable amounts of higher-nuclear MDA grades in addition to the desired diamines, which are then phosgenated together with the diamines. In order to obtain the diisocyanates from the mixture of diisocyanates and polyisocyanates (binuclear MDI and higher-nuclear MDI grades), the diisocyanates have to be distilled out of the mixture of diisocyanates and polyisocyanates (monomer/polymer separation). After this monomer separation, the isomers must be separated from one another by distillation and/or crystallization, involving the use of large amounts of equipment and high energy consumption. The laboriously separated isomers are then mixed together again in high-monomer-content finished products.

The crude monomer distillate (crude monomer, consisting substantially of diisocyanate) obtained by monomer/polymer separation in the process according to the prior art still contains undesirably high concentrations of secondary components, however. For example, this crude MDI monomer mixture contains many times the maximum concentration of 50 ppm monochlorobenzene and a maximum of 20 ppm phenyl isocyanate, preferably a maximum of 20 ppm monochlorobenzene and a maximum of 10 ppm phenyl isocyanate commonly demanded by polyurethane manufacturers. In addition, conventional crude MDI monomer mixture contains a considerable amount of uretdione (dimeric para-MDI), which in larger concentrations leads to product turbidity and solids precipitation in the MDI. The diisocyanates distilled off in the monomer/polymer separation must therefore be freed from secondary components in subsequent distillation stages involving considerable cost and effort.

Special MDI grades with specified contents of isomers, in other words 2,4'-MDI, 2,2'-MDI and 4,4'-MDI, are traded commercially. According to the prior art the compositions corresponding to the commercially available MDI grades with the low secondary component contents are therefore produced by complex, multistage isomer separation by means of distillation and/or crystallization. The isocyanate composition required for a specific application is then produced by blending these MDI grades.

For many applications of MDI grades, however, polymer production does not require a very high 4,4'-MDI purity, in other words a very low 2,2'-MDI content, for example, in the feedstocks to be blended. The use of a pure 4,4'-MDI grade with very low 2,2'-MDI contents produced by means of several complex distillation stages for mixing with other MDI grades to produce an isocyanate composition that is suitable for the specific application is therefore unsatisfactory in terms of energy consumption.

The following is also known from the prior art:

The following two works, for example, describe the direct production of mixed MDI products by means of a selective MDA synthesis. Keggenhoff, Maehlmann & Eifler (EP-158059 B1) produced an MDA mixture with a high 4,4'-MDA content, containing approximately 80% 4,4'-MDA and approximately 10% 2,4'-MDA, and a binuclear content of approximately 90%. By contrast, Eifler & Ellendt (EP-3303 B1) were able to produce a high-monomer-content MDA with 88% binuclear content, containing 19% 2,2'-MDA, 36% 2,4'-MDA and 45% 4,4'-MDA. High molar ratios of aniline/formaldehyde of over 8 are needed to produce these products, which means that large amounts of aniline have to be recycled. In addition, high consumptions of HCl (for catalysis) and NaOH (to neutralize the catalyst) are necessary for many of these grades. Products having above all a high 4,4'-MDA content display a very high specific HCl catalyst consumption. The production of high 2,4'-MDI-content, monomer-rich MDA grades in particular leads to a high, often undesirable secondary yield of 2,2'-MDI. High concentrations of 2,2'-MDI are undesirable in many applications because of its low reactivity.

The production of polymeric and monomeric MDI products is generally known in the literature. The production of polymeric MDA with binuclear contents of 46 to 65% can take place, for example, in accordance with DE-2750975 A1 or DE-2517301 A1. The two processes of distillation (DE-3145010 A1) and crystallization (EP-A-482490) that are predominantly used in industry for isomer separation in the MDI monomers are described in detail in the literature. None of the works, however, describes the direct use of the crude monomeric MDI fraction from the monomer/polymer separation as a feedstock source for MDI blends. The people skilled in the art concentrate instead on the most economical production possible of ultrapurified monomeric isomer mixtures containing >98% 4,4'-MDI and a mixture of approximately 50% each of 2,4'- and 4,4'-MDI, which can optionally contain up to 2.5% 2,2'-MDI (M. Stepanski, P. Faessler: "New hybrid process for purification and separation of MDI isomers", Sulzer Chemtech, Presentation at the Polyurethanes Conference 2002 in Salt Lake City, October/2002).

The production of high-monomer-content MDI mixtures by blending polymeric MDI products and repeatedly distilled monomeric products is a common process in the polyurethane industry. For example, it is used in the production of low-viscosity blended MDI products in U.S. Pat. No. 5,258,417.

The purification of crude, polymeric MDI mixtures has been examined in principle in many works. For example, attempts are made to remove impurities using chemical additives (U.S. Pat. Nos. 3,925,437, U.S. Pat. No. 3,793,362, DE-A-2316028). In DD-A-118,105 and GB-A-1,114,690, solvents are added in an attempt to remove chemically bonded impurities. DD-A-271,820 suggests stripping MDI and TDI (toluene diisocyanate), which causes a marked feedstock decomposition of 0.1 to 10 wt. %, however, and substantially pursues the objective of removing very stubborn, chemically bonded impurities.

U.S. Pat. No. 3,857,871 discloses a stripping process for polymeric MDI which leads to a reduction in acidity and hydrolyzable chlorine in the product. GB-A-1,362,708 describes a process for the purification of polymeric MDI, which admittedly reduces the amount of hydrolyzable chlorine significantly. The product still contains 0.1% solvent, however.

SUMMARY OF THE INVENTION

The object of the present invention is therefore to provide a simple and energy-saving process for the production of high-monomer-content MDI mixtures and a process for the production of MDI mixtures with a desired ratio of MDI isomers, which contains a very low proportion of secondary components, particularly in terms of the solvent, phenyl isocyanate, uretdione and phosgene.

This object is achieved by separating off from a crude diisocyanate and polyisocyanate mixture a fraction containing at least 95 wt. % binuclear methylenediphenyl diisocyanate composed of over 60 wt. % 4,4'-MDI, 4–35 wt. % 2,4'-MDI and 0.1–10 wt. % 2,2'-MDI and a maximum of 20 ppm phenyl isocyanate in a single distillation step.

DETAILED DESCRIPTION OF THE INVENTION

Figure 1:
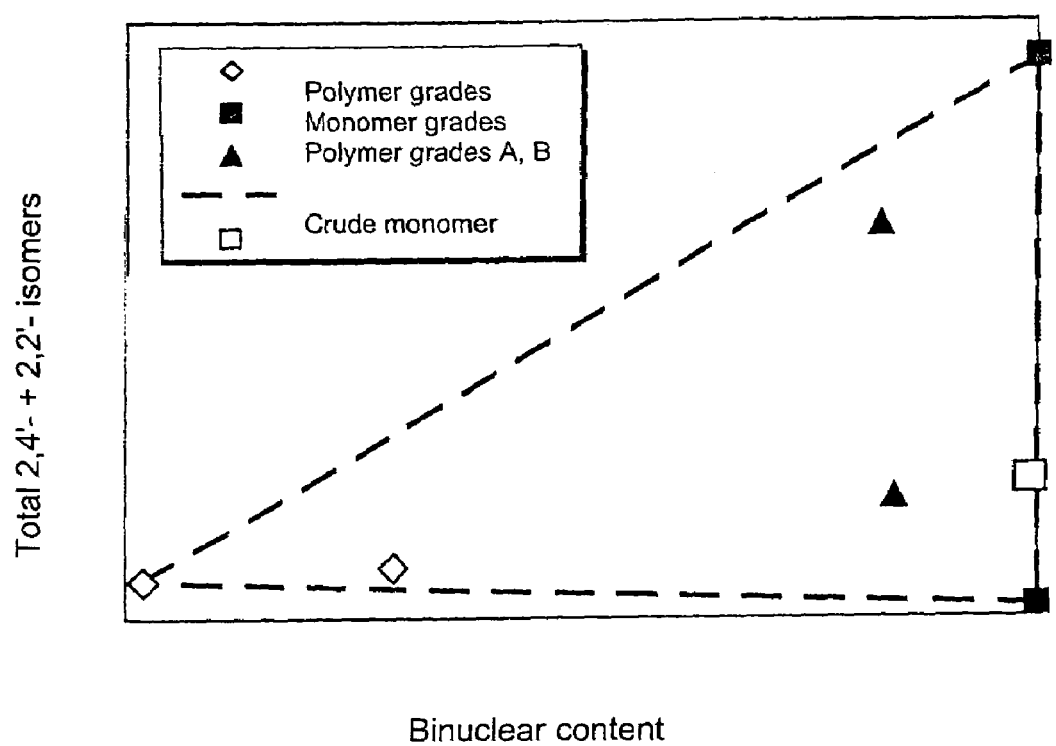
FIG. 1 is a schematic representation of the binuclear content of some commercially available starting materials for the production of MDI blends.

The invention relates to a process for the production of a fraction of diisocyanates from the diphenylmethane series containing at least 95 wt. % binuclear methylenediphenyl diisocyanate, in which a) aniline and formaldehyde are reacted in the presence of an acid catalyst to produce diamines and polyamines of the diphenylmethane series containing binuclear methylenediphenyl diamine, b) the diamines and polyamines of the diphenylmethane series containing binuclear methylenediphenyl diamine are phosgenated, optionally in the presence of a solvent, to give a crude diisocyanate and polyisocyanate, and c) a fraction containing at least 95 wt. % binuclear methylenediphenyl diisocyanate having a 4,4'-MDI content of over 60 wt. %, a 2,4'-MDI content of from 4 to 35 wt. % and a 2,2'-MDI content of from 0.01 to 10 wt. %, relative to the mass of the fraction, and a maximum of 20 ppm phenyl isocyanate and optionally a maximum of 50 ppm solvent, is separated off from the crude diisocyanate and polyisocyanate in a single distillation step with optional upstream and/or downstream separation of low-boiling components.

In step c), a fraction containing at least 99 wt. % binuclear methylenediphenyl diisocyanate with a 4,4'-MDI content of over 76 wt. %, a 2,4'-MDI content of from 5 to 22 wt. % and a 2,2'-MDI content of from 0.2 to 3 wt. %, relative to the mass of the fraction, and a maximum of 10 ppm phenyl isocyanate and optionally a maximum of 20 ppm solvent, is preferably separated off from the crude diisocyanate and polyisocyanate.

The stated maximum concentrations of phenyl isocyanate and solvent are relative to the mass of the entire separated fraction.

Separation of the fraction in a single distillation step means that the separated MDI is evaporated completely in this single distillation step alone and is condensed again and obtained as a fraction at another part of the column. In the optional upstream and/or downstream separation of low-boiling components, by contrast, predominantly low-boiling components are separated off by evaporation and subsequent condensation. Most of the MDI is not evaporated during separation of the low-boiling components.

Separation of the fraction in a single distillation step therefore also means, in particular, that in the process according to the invention, after separation of the fraction from the crude diisocyanate and polyisocyanate in the single distillation step, substantially no further separation of the isomeric MDI diisocyanates occurs.

By the process according to the invention, high-monomer-content MDI mixtures with a high binuclear MDI content of at least 95 wt. % relative to the mass of the fraction and with low proportions of secondary components can be obtained with significantly lower energy consumption than in prior art separation processes. The energy consumption is reduced here in comparison to the processes according to the prior art since the condensation of aniline and formaldehyde with large excesses of aniline and its subsequent distillation and recycling are avoided. At the same time, however, by the process according to the invention, in the distillation of the mixture of diisocyanates and polyisocyanates deriving from the phosgenation, the amount of undesirable secondary components is reduced in only one distillation step, making subsequent distillation steps unnecessary. Isomer separation by multistage distillation, wherein the undesirable secondary components are removed at the same time (according to the prior art), is avoided in the process according to the invention.

In the distillation of MDI isomers according to the prior art, considerable technical effort is also devoted to destroying trace components such as hydrolyzable chlorine components. Such trace components do not constitute a nuisance in high-monomer-content MDI mixtures, however. In order to remove the remaining trace components, monomeric MDI is typically evaporated and condensed around 4 to 6 times during isomer distillation before it can be sold as pure 4,4'-MDI. In contrast, the energy consumption for production of a low-solvent crude monomeric MDI in accordance with the present invention is markedly lower because the MDI is produced in a single distillation step with optional upstream and/or downstream separation of low-boiling components.

Production of the high-monomer-content MDI fraction with a high binuclear MDI content of at least 95 wt. % relative to the mass of the fraction by the process according to the invention is achieved by removing the troublesome low-boiling secondary components such as phenyl isocyanate and optionally solvent at the monomer/polymer separation stage. This separation in the single distillation step in step c) is preferably carried out at absolute pressures of from 1 to 50 mbar at the head of the distillation column and at temperatures of from 100° C. to 300° C. Removal of the secondary components during production of the fraction containing at least 95 wt. % binuclear methylenediphenyl diisocyanate and a maximum of 20 ppm phenyl isocyanate and optionally a maximum of 50 ppm solvent by the process according to the invention can be supported by stripping the crude MDI monomer mixture obtained during distillation (monomer/polymer separation) or by removing the low-boiling components prior to the actual monomer/polymer separation.

Stripping the crude MDI monomer mixture obtained during distillation (monomer/polymer separation) involves separating off the low-boiling components comprising solvent, phenyl isocyanate and, for example, small residual amounts of phosgene at the head of a stripping column with a small split stream of MDI isomers. The separated low-boiling fraction can be returned to the MDI/solvent separation stage or preferably supplied to a separate low-boiling component separating column, freed from solvent and phenyl isocyanate and recycled as additional MDI feedstock or used separately.

If separation of the low-boiling components by stripping is omitted, the monomer/polymer separation stage can be designed as a distillation column with side stream removal. Here the clean MDI monomer mixture can be separated off in the side stream of the column and the low-boiling components at the head of the column. The low-boiling components can be recycled or preferably freed from solvent and phenyl isocyanate in a separate low-boiling component separating column.

The removal of low-boiling components can also be improved so that virtually no phenyl isocyanate or solvent is supplied to the monomer/polymer separation stage. This is achieved, for example, by returning the distillates from the optionally multistage solvent removal process to the first solvent separation stage ahead of monomer/polymer separation.

Crystallization can also be a suitable process for purifying the crude MDI monomer mixture.

In this process, the product obtained from the distillation column by monomer/polymer separation is preferably cooled to a temperature of 35 to 80° C. by rapid quench cooling in order to keep down the content of uretdione. Suitable processes for the quench cooling of the continuous MDI monomer stream already exist in the prior art. For example, a circulation system with a circulating pump and heat exchanger at a temperature of, e.g., 60° C. is suitable for cooling the hot product from around 140 to 200° C. to 60° C. in the shortest time, thereby keeping uretdione formation to a minimum.

The invention also relates to a process for the production of mixtures containing diisocyanates from the diphenylmethane series, in which a) a fraction containing at least 95 wt. % binuclear methylenediphenyl diisocyanate with a 4,4'-MDI content of over 60 wt. %, a 2,4'-MDI content of 4 to 35 wt. % and a 2,2'-MDI content of 0.01 to 10 wt. %, relative to the mass of the fraction, and a maximum of 20 ppm phenyl isocyanate and optionally a maximum of 50 ppm solvent, is produced by the above-described process, and b) the fraction produced in step a) is blended with one or more mixtures containing diisocyanates and/or polyisocyanates of the diphenylmethane series.

The fraction of diisocyanates from the diphenylmethane series containing at least 95 wt. % binuclear MDI produced by the process according to the invention can be used for blending with higher-nuclear (polymeric) MDI and the commercially available MDI grades to produce any MDI mixture with freely adjustable proportions of binuclear MDI and higher-nuclear MDI and freely adjustable proportions of the various MDI isomers.

Figure 2:
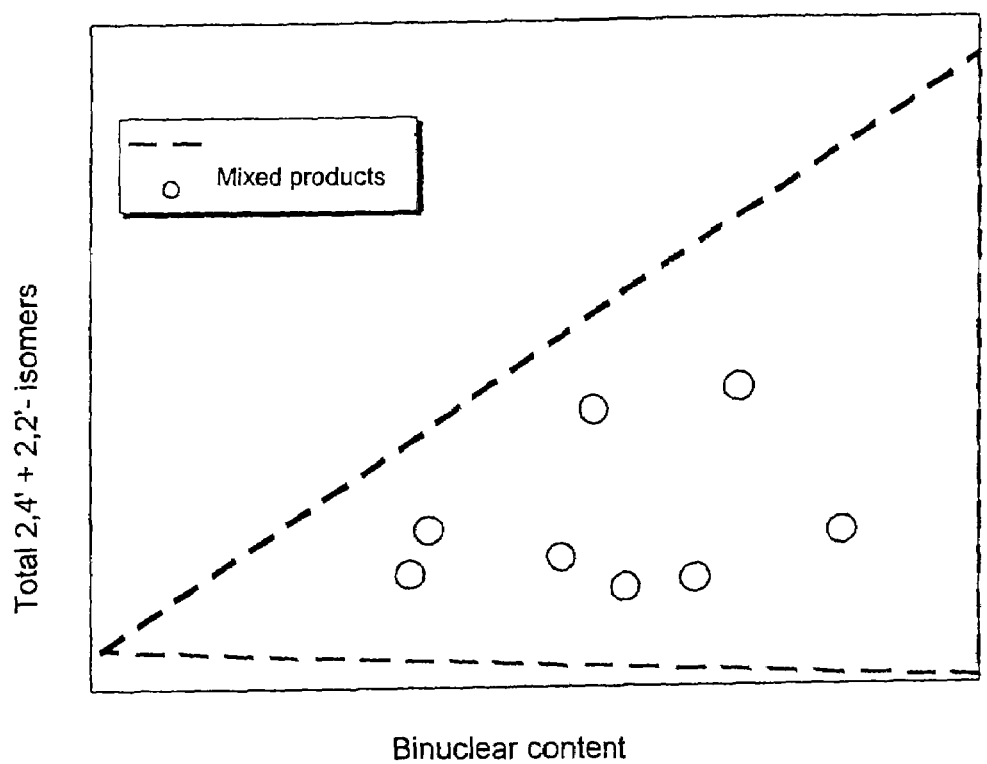
FIG. 2 is a schematic representation of the binuclear content of some blended MDI products.

The fractions of diisocyanates of the diphenylmethane series produced by the process according to the invention have a preferred composition as follows:

Total binuclear content: ≧95 wt. %
4,4'-MDI content: >60 wt. %, relative to the total fraction,
2,4'-MDI content: 4 wt. % to 35 wt. %, relative to the total fraction,
2,2'-MDI content: 0.01 wt. % to 10 wt. %, relative to the total fraction,
Solvent content: 0 to 50 ppm, relative to the total fraction,
Phenyl isocyanate content: 0 to 20 ppm, relative to the total fraction,
Uretdione content: 0 to 0.5 wt. %, relative to the total fraction Particularly preferred fraction compositions are as follows:

Total binuclear content: ≧99 wt. %
4,4'-MDI content: >76 wt. %, relative to the total fraction,
2,4'-MDI content: 5 wt. % to 22 wt. %, relative to the total fraction,
2,2'-MDI content: 0.2 wt. % to 3 wt. %, relative to the total fraction,
Solvent content: 0 to 20 ppm, relative to the total fraction,
Phenyl isocyanate content: 0 to 10 ppm, relative to the total fraction,
Uretdione content: 0 to 0.1 wt. %, relative to the total fraction The fractions of diisocyanates from the diphenylmethane series containing at least 95 wt. % binuclear MDI produced by the process according to the invention can be blended with polyisocyanates or other organic isocyanates. FIG. 1 provides a schematic view of some commercially available starting products for the production of MDI blends. FIG. 2 shows some examples of blended products from the MDI series in the same parameter region. The horizontal axis describes the total binuclear content, the vertical axis the total ortho-binuclear contents (2,2'-MDI+2,4'-MDI). The dashed line encloses the triangle within which blends can be produced from the specified starting products.

The fractions of diisocyanates of the diphenylmethane series containing at least 95 wt. % binuclear MDI produced by the process according to the invention can be blended with one or more mixtures containing aromatic isocyanates. In addition to the previously mentioned mixtures containing diisocyanates and/or polyisocyanates of the diphenylmethane series that are preferably used, mixtures containing toluene diisocyanate (e.g., 2,4-TDI, 2,6-TDI) or mixtures containing naphthalene diisocyanate (e.g., 1,5-NDI) or mixtures of these isocyanates can also preferably be used. In principle, however, other aromatic and/or aliphatic mono-, di-, tri- or higher-functional isocyanates can also be used for blending.

The fractions of diisocyanates of the diphenylmethane series containing at least 95 wt. % binuclear MDI produced by the process according to the invention and the blended products produced from them can be used for the conventional isocyanate modification reactions, such as: carbodiimidization and resulting uretonimines, or for the production of prepolymers from OH-functional polyesters, $C_2$, $C_3$ and/or $C_4$ polyethers, uretdiones, allophanates, biurets and/or urea derivatives.

The fractions of diisocyanates of the diphenylmethane series containing at least 95 wt. % binuclear MDI produced by the process according to the invention can be used as mixing components with other diisocyanates and polyisocyanates of the MDI series and/or other isocyanates for the production of isocyanate components for use in the production of polymers. The finished parts to be produced from these blended products cover the entire field of polyurethane chemistry. The following are cited by way of example:

Rigid foams for the insulation and refrigerator industry
Packaging foam
Flexible foam and flexible molded foam for furniture and the automotive industry
Coatings, adhesives, sealants, and elastomers applications
Semi-rigid Polyurethane foams The blended MDI products produced according to the invention can be produced with the use of much less equipment and lower energy consumption for distillation at the MDI isomer separation stage or for aniline distillation at the MDA stage. At the same time, the average HCl and NaOH feedstock consumption at the MDA stage can be significantly reduced if the use of polymer A or polymer B grades, which are produced according to the prior art with large specific amounts of HCl (to control isomer distribution in the MDA) and NaOH, can be avoided.

In many blended products, the content of 2,2'-MDI can also be reduced if polymer B grades with high 2,2'-MDI contents are no longer produced directly and used as mixing components for high-monomer-content end products. By using low-2,2'-MDI grades of MDI in the blend, such as the fraction produced by the process of the present invention with only low 2,2'-MDI contents, MDI products with significantly lower 2,2'-MDI contents and hence improved reactivity can be produced by blending. The polymers produced from them also display improved polymer properties.

EXAMPLES

The solution to the inventive object described is explained by reference to the following examples. All % values stated are relative to weight (wt. %).

The following MDI feedstocks with the stated composition can be used for the production of commercial MDI mixtures (MCB=monochlorobenzene solvent, PHI=phenyl isocyanate):

| Grade | 2,2'-MDI | 2,4'-MDI | 4,4'-MDI | Total binuclear | MCB | PHI |
|---|---|---|---|---|---|---|
| Polymer grade (200 mPas) | <0.2% | 3% | 39% | 42% | <10 ppm | <8 ppm |
| 4,4'-pure grade | 0% | 1.5% | 98.5% | 100% | <10 ppm | <8 ppm |
| 2,4'-rich grade | <2% | 55% | 44% | 100% | <10 ppm | <8 ppm |
| 2,2'-rich grade | 50% | 50% | 0% | 100% | <10 ppm | <8 ppm |

-continued

| Grade | 2,2'-MDI | 2,4'-MDI | 4,4'-MDI | Total binuclear | MCB | PHI |
|---|---|---|---|---|---|---|
| Polymer A grade | 0.7% | 11% | 78% | 90% | <10 ppm | <8 ppm |
| Polymer B grade | 6% | 31% | 51% | 88% | <10 ppm | <8 ppm |
| Crude monomer | 0.7% | 11% | 88% | >99% | 250 ppm | 44 ppm |
| Pure crude monomer* | 0.7% | 11% | 88% | >99.5% | 15 ppm | 8 ppm |

*fraction produced by the process according to the invention

The two polymer grades A and B are produced with high aniline excesses and thus require complex and expensive distillation and recycling of the aniline. The MDI isomer distillation products, 4,4'-pure, 2,4'-rich and 2,2'-rich grades, on the other hand, have to be produced by extremely complex, multistage distillation of the mixture of diisocyanates and polyisocyanates deriving from the phosgenation in order to separate off the undesirable secondary components and to establish the required specifications for the individual binuclear MDI isomers (2,4'-MDI, 2,2'-MDI and 4,4'-MDI).

The polymer grade and the crude monomer grades (crude monomer and pure crude monomer), on the other hand, can be obtained from the mixture of diisocyanates and polyisocyanates obtained from the phosgenation with little effort and low energy consumption by a single distillation. The polymer grade is produced here as a bottom product and contains large proportions of higher-nuclear MDI. The crude monomer grades are drawn off at the head of the distillation column or as a side discharge. Crude monomer and pure crude monomer differ in that pure crude monomer was produced by the process according to the invention and therefore displays only very low residual proportions of secondary components such as phenyl isocyanate and optionally, solvent, and thus requires no additional processing by distillation.

Example 1 (Comparative)

Production of a mixed MDI product from 17 wt. % polymer grade, 51 wt. % polymer grade A and 32 wt. % polymer grade B resulted in the following product quality (MCB=monochlorobenzene as solvent)

| Grade | 2,2'-MDI | 2,4'-MDI | 4,4'-MDI | Total binuclear MDI | MCB |
|---|---|---|---|---|---|
| Blend 1 | 3.9% | 16.3% | 62.5% | 82.7% | <10 ppm |

Although a precision-distilled product (4,4'-pure grade, 2,2'-rich grade, 2,4'-rich grade) was not used to produce Blend 1, 83 wt. % of polymer grades A and/or B, produced using very complex methods, had to be used instead. The production of Blend 1 according to Example 1 was therefore very energy intensive.

Example 2 (Comparative)

Production of a mixed MDI product from 36.4% polymer grade, 37.1% 4,4 grade and 26.5% 2,4 grade resulted in the following product quality:

| Grade | 2,2'-MDI | 2,4'-MDI | 4,4'-MDI | Total binuclear MDI | MCB |
|---|---|---|---|---|---|
| Blend 2 | 0.3% | 16.3% | 62.5% | 79.1% | <10 ppm |

Although the production of Blend 2 required no elaborately produced polymer MDA grade A or B or phosgenated product (polymer grade A and B), 64 wt. % of 4,4'-pure and 2,4'-rich grades, produced using very complex methods, had to be used instead. The production of Blend 2 according to Example 2 was therefore very energy intensive. Compared to Blend 1, however, it had a significantly lower 2,2'-MDI content.

Example 3 (Comparative)

Production of a mixed MDI product from 35.9% polymer grade, 45.7% crude monomer, 18.3% 2,4 grade resulted in the following product quality

| Grade | 2,2'-MDI | 2,4'-MDI | 4,4'-MDI | Total binuclear MDI | MCB | PHI |
|---|---|---|---|---|---|---|
| Blend 3 | 0.56% | 16.3% | 62.5% | 79.4% | 114 ppm | 22 ppm |

Example 3 shows that Blend 3 cannot meet the important customer requirement regarding solvent content (<20 ppm) and PHI content (<10 ppm), which was met with Blend 2 (Example 2). A low 2,2'-MDI content comparable to that obtained in Example 2 can be achieved, however.

Example 4 (According to the Invention)

Production of a mixed MDI product from 35.9% polymer grade, 45.7% pure crude monomer, 18.3% 2,4 grade resulted in the following product quality

| Grade | 2,2'-MDI | 2,4'-MDI | 4,4'-MDI | Total binuclear MDI | MCB | PHI |
|---|---|---|---|---|---|---|
| Blend 4 | 0.56% | 16.3% | 62.5% | 79.4% | <10 ppm | <8 ppm |

Only around 18% of energy-intensive precision-distilled isomer product was required for the production of this blend, which meant a reduction in the use of precision-distilled isomer products by around 70%. The two polymer grades A and B obtained from MDA production using very complex methods can be omitted altogether. A product comparable in quality to that obtained in Example 2 was produced, with only a slight, uncritical increase in 2,2' content.

Example 5 (According to the Invention)

If the high 2,2' content of 3.9 wt. % is actually required, an additionally available product quality (2,2'-rich type) containing approximately 50% 2,2'-MDI and approximately 50% 2,4'-MDI can be used as the fourth component. The starting values from Example 1 can be reproduced exactly in this way.

Production of a mixed MDI product from 30.2% polymer grade, 51.8% pure crude monomer, 11.4% 2,4 grade and 6.7% 2,2 grade resulted in the following product quality

| Grade | 2,2'-MDI | 2,4'-MDI | 4,4'-MDI | Total binuclear MDI | MCB | PHI |
|---|---|---|---|---|---|---|
| Blend 5 | 3.9% | 16.3% | 62.5% | 82.7% | <10 ppm | <8 ppm |

Only around 18% of precision-distilled product (2,2'-rich grade and 2,4'-rich grade) was needed for the production of Blend 5. The elaborately produced polymer grades A and B can be omitted altogether. This results in a reduction in the amount of energy-intensively produced raw materials of around 80% in comparison to Example 1.

Example 6 (Comparative)

1000 g of aniline were mixed with 306 g of 31.9% aqueous HCl in a stirred-tank reactor at 40° C. 480 g of 32% formaldehyde solution were added dropwise within 15 minutes. Stirring was first continued for a further 15 min at 40° C. and the temperature slowly increased to 100° C. over the next 2.5 h. The reaction mixture was then refluxed with stirring at 100° C. for 10 h and neutralized with 50% sodium hydroxide solution, the aqueous phase separated off and the organic phase rinsed with water. The organic solution was removed and freed from excess aniline by distillation in vacuo. The MDA reaction product was poured into a second stirred-tank reactor containing an ice-cold 15% solution of phosgene in monochlorobenzene (MCB); the molar excess of phosgene was 150%. The reaction solution was slowly heated to 100° C. over one hour with continuous addition of 40 liters/h of phosgene. Over the space of a further hour, the mixture was brought to boiling point, the phosgene addition stopped and a vacuum applied. The temperature was gradually increased to 210° C., the pressure reduced to 3 mbar and the solvent removed completely. A crude MDI mixture containing 58 wt. % monomeric MDI (comprising 0.21 wt. % 2,2'-MDI, 5.1 wt. % 2,4'-MDI, 52.7 wt. % 4,4'-MDI), 65 ppm MCB and 14.5 ppm PHI was obtained.

The crude MDI mixture was broken down into the polymeric MDI product and the crude monomer fraction (binuclear MDI). A glass column having a product feed into the bottoms evaporator below it was used as the experimental set-up; instead of separating floors the column contained only droplet separator packing. The distillate was precipitated completely at the head and removed. The head pressure was adjusted to 5 mbar by means of a vacuum pump.

The stream of 500 g/h crude MDI mixture was supplied at 180° C. to the continuously operated equipment. Following a feed phase of 2 h, the following material flows were removed from the equipment as products:

Bottom of the distillation equipment: 62 g in 10 min with the following composition:

0.09% 2,2'-MDI, 3.7% 2,4'-MDI, 39.8% 4,4'-MDI, 0.5 ppm MCB, 4 ppm PHI, remainder: polymeric MDI (viscosity of bottoms at 25° C.: 185 mPas).

Head stream from the distillation equipment: 21 g in 10 min with the following composition:
0.57% 2,2'-MDI, 9.0% 2,4'-MDI, 89.3% 4,4'-MDI, 241 ppm MCB, 44 ppm PHI All % values for the compositions relate to the weight of the individual complete sample.

Example 7 (According to the Invention)

The crude MDI mixture from Example 6 was broken down into the polymeric MDI product and the clean pure crude monomer and a low-boiling component fraction.

A glass column with a product feed to the bottoms evaporator and stainless steel distillation packing with 4 theoretical separation stages, the liquid backflow from the head of the laboratory column being able to be removed and returned in part to the column as a reflux, was used as the experimental set-up. The distillate was completely precipitated at the head and 95% was returned to the column as a reflux using a sample divider. The head pressure was set to 5 mbar by means of a vacuum pump.

The stream of 500 g/h crude MDI mixture was supplied at 180° C. to the continuously operated equipment. Following a feed phase of 2 h, the following material flows were removed from the equipment as products:

Bottom of the distillation equipment: 60 g in 10 min with the following composition:

0.08% 2,2'-MDI, 3.6% 2,4'-MDI, 39.9% 4,4'-MDI, 0.5 ppm MCB, 4 ppm PHI, remainder: polymeric MDI (viscosity of bottoms at 25° C.: 205 mPas).

Head stream from the distillation equipment: 2 g in 10 min with the following composition:

2.0% 2,2'-MDI, 17.0% 2,4'-MDI, 80.7% 4,4'-MDI, 730 ppm MCB, 380 ppm PHI.

Side stream from the distillation equipment between the two separating packing elements (corresponds to the pure crude monomer fraction): 19 g in 10 min with the composition 0.45% 2,2'-MDI, 8.7% 2,4'-MDI, 90.7% 4,4'-MDI, 12 ppm MCB, 6 ppm PHI.

All % values for the compositions relate to the weight of the individual complete sample.

The above Examples show that the production of blended products from the pure crude monomer produced by the process according to the invention offers decisive advantages in comparison to the prior art:

The contents of 2,2'-MDI in the blended product can be significantly reduced by replacing the polymer grades A and B with pure crude monomer in the blend, which increases the reactivity and reduces the residual monomer contents.

The contents of solvents such as MCB, phenyl isocyanate and phosgene in the blended product can be significantly reduced by replacing crude monomer with pure crude monomer in the blend. This significantly improves the purity of the blended products and hence their properties.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a fraction of diisocyanates of the diphenylmethane series containing at least 95 wt. % binuclear methylenediphenyl diisocyanate comprising:

a) reacting aniline and formaldehyde in the presence of an acid catalyst to produce diamines and polyamines of the diphenylmethane series containing binuclear methylenediphenyl diamine, b) phosgenating the diamines and polyamines of the diphenylmethane series containing binuclear methylenediphenyl diamine to produce a crude diisocyanate and polyisocyanate, and c) separating from the crude diisocyanate and polyisocyanate a fraction containing at least 95 wt. % binuclear methylenediphenyl diisocyanate comprising greater than 60 wt. % 4,4'-MDI, from 4 to 35 wt. % 2,4'-MDI, from 0.01 to 10 wt. % 2,2'-MDI relative to the mass of the fraction, and no more than 20 ppm phenyl isocyanate in a single distillation step.

2. The process of claim 1 in which step b) is carried out in the presence of a solvent.

3. The process of claim 2 in which no greater than 50 ppm of solvent are present in the fraction separated in step c).

4. The process of claim 1 in which low-boiling material is removed before and/or after separating the fraction in step c).

5. The process of claim 1 in which a fraction containing at least 99 wt. % binuclear methylenediphenyl diisocyanate comprising greater than 76 wt. % 4,4'-MDI, from 5 to 22 wt. % 2,4'-MDI and from 0.2 to 3 wt. % 2,2'-MDI relative to the mass of the fraction, and a maximum of 10 ppm phenyl isocyanate is separated in step c).

6. The process of claim 2 in which no more than 20 ppm solvents are present in the fraction separated in step c).

7. A process for the production of a diphenymethane diisocyanate mixture comprising blending the fraction separated in step c) of claim 1 with a mixture containing an aromatic isocyanate.

8. The process of claim 7 in which the fraction separated in step c) of claim 1 is blended with a mixture containing a diisocyanate and/or polyisocyanate of the diphenylmethane series.

9. The process of claim 7 in which the fraction separated in step c) of claim 1 is blended with a mixture containing toluene diisocyanate.

10. The process of claim 7 in which the fraction separated in step c) of claim 1 is blended with a mixture containing naphthalene diisocyanate.

11. A process for the production of a polymer comprising:

(a) reacting the fraction separated in step c) of claim 1 and/or the blend produced according to any of claims 7 to 10 with (b) a polyol.

* * * * *